| (12) | United States Patent | (10) Patent No.: | US 8,803,957 B2 |
|---|---|---|---|
| | Makiyama et al. | (45) Date of Patent: | Aug. 12, 2014 |

(54) IMAGE PICKUP UNIT AND ENDOSCOPE

(71) Applicant: Olympus Medical Systems Corp., Tokyo (JP)

(72) Inventors: Satoshi Makiyama, Hino (JP); Takehiko Iguchi, Hino (JP); Shinya Kono, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/958,807

(22) Filed: Aug. 5, 2013

(65) Prior Publication Data

US 2013/0314517 A1 Nov. 28, 2013

Related U.S. Application Data

(63) Continuation of application No. PCT/JP2012/076126, filed on Oct. 9, 2012.

(30) Foreign Application Priority Data

Oct. 13, 2011 (JP) ................................. 2011-226147

(51) Int. Cl.
| *A62B 1/04* | (2006.01) |
|---|---|
| *A61B 1/00* | (2006.01) |
| *G02B 23/24* | (2006.01) |
| *G03B 37/00* | (2006.01) |
| *A61B 1/045* | (2006.01) |
| *A61B 1/05* | (2006.01) |
| *H04N 5/232* | (2006.01) |
| *H02K 41/035* | (2006.01) |
| *G01N 21/954* | (2006.01) |

(52) U.S. Cl.
CPC ............ *H04N 5/232* (2013.01); *A61B 1/00188* (2013.01); *G02B 23/2476* (2013.01); *G03B 37/005* (2013.01); *A61B 1/045* (2013.01); *A61B 1/05* (2013.01); *G01N 21/954* (2013.01); *H02K 41/0356* (2013.01)
USPC .......................................................... 348/65

(58) Field of Classification Search
None
See application file for complete search history.

(56) References Cited

U.S. PATENT DOCUMENTS

| 6,036,637 | A | * | 3/2000 | Kudo ............................ 600/173 |
|---|---|---|---|---|
| 8,343,042 | B2 | * | 1/2013 | Leiner et al. .................. 600/167 |
| 2009/0303619 | A1 | * | 12/2009 | Iwasaki et al. ................ 359/811 |

FOREIGN PATENT DOCUMENTS

| JP | 2002-214504 A | 7/2002 |
|---|---|---|
| JP | 2008-110061 A | 5/2008 |
| JP | 2009-015224 A | 1/2009 |
| JP | 2010-046424 A | 3/2010 |

OTHER PUBLICATIONS

International Search Report dated Jan. 15, 2013 issued in PCT/JP2012/076126.

* cited by examiner

*Primary Examiner* — Mehrdad Dastouri
*Assistant Examiner* — James Anderson, II
(74) *Attorney, Agent, or Firm* — Scully, Scott, Murphy & Presser, P.C.

(57) ABSTRACT

The present invention provides an image pickup unit including an objective lens including a plurality of optical system members via which an object image is formed, the image pickup unit including: a fixed barrel that holds a fixed lens in the objective lens; a moving lens holding barrel that holds a moving lens and is disposed so as to be slidable along an optical axis inside the fixed barrel; and a voice coil motor section that generates a drive force for moving the moving lens holding barrel relative to the fixed barrel along the optical axis, and the voice coil motor section is disposed so that a center axis of action of a generated thrust force passes through a gravity center of a driven member to be driven by the voice coil motor section.

6 Claims, 8 Drawing Sheets

IMAGE PICKUP UNIT AND ENDOSCOPE

CROSS REFERENCE TO RELATED APPLICATION

This application is a continuation application of PCT/JP2012/076126 filed on Oct. 9, 2012 and claims benefit of Japanese Application No. 2011-226147 filed in Japan on Oct. 13, 2011, the entire contents of which are incorporated herein by this reference.

BACKGROUND OF THE INVENTION

1. Field of the Invention

The present invention relates to an image pickup unit including an objective lens that includes a moving lens, and an endoscope.

2. Description of the Related Art

In order to observe sites that are difficult to observe such as an inside of a living body or an inside of a structure, endoscopes that can be introduced from an outside to the inside of the living body or the structure, the endoscopes including an image pickup unit for picking up an optical image, have been used in, for example, medical fields and industrial fields.

An image pickup unit of an endoscope includes an objective lens via which an object image is formed, and an image pickup device, such as a CCD (charge coupled device) or a CMOS (complementary metal-oxide film semiconductor) sensor, disposed at a plane on which an image from the objective lens is formed.

For example, Japanese Patent Application Laid-Open Publication No. 2008-110061 discloses a shooting unit for an endoscope, the shooting unit including a moving lens and having a function that changes an image magnification (scaling function or zoom function). The shooting unit disclosed in Japanese Patent Application Laid-Open Publication No. 2008-110061 has a configuration in which a moving lens holding barrel that holds a moving lens in an objective lens group is disposed so as to freely advance/retract in an optical axis direction and the moving lens holding barrel is moved by an electric linear actuator so as to advance/retract, the electric linear actuator being provided so as to project at an outer peripheral portion of the shooting unit.

SUMMARY OF THE INVENTION

An image pickup unit according to an aspect of the present invention provides an image pickup unit including an objective lens including a plurality of optical system members via which an object image is formed, the image pickup unit including: a moving lens including one or more lenses, the moving lens forming a part of the objective lens; a fixed lens holding barrel that holds the optical system members other than the moving lens in the objective lens; a cylindrical fixed barrel fixed to the fixed lens holding barrel with an optical axis of the objective lens as a center axis; a moving lens holding barrel that holds the moving lens and is disposed so as to be slidable along the optical axis inside the fixed barrel; a voice coil motor section that generates a drive force for moving the moving lens holding barrel relative to the fixed barrel along the optical axis; a position detection magnet fixed to the moving lens holding barrel; and a magnetism detecting section whose position relative to the fixed barrel is fixed, the magnetism detecting section detecting magnetism of the position detection magnet, wherein the voice coil motor section is disposed so that a center axis of action of a generated thrust force passes through a gravity center of a driven member to be driven by the voice coil motor section; wherein the objective lens is configured so that an image magnification thereof is changed as a result of the moving lens holding barrel being moved in the optical axis direction and as the moving lens holding barrel becomes closer to one end of a movable range, the magnification becomes lower; wherein the voice coil motor section includes a coil wound on a periphery of the moving lens holding barrel around the optical axis, and a permanent magnet fixed to the fixed barrel; and wherein the position detection magnet is disposed so as to bias the moving lens holding barrel toward the one end of the movable range via a magnetic force between the position detection magnet and the permanent magnet.

Also, an endoscope according to an aspect of the present invention includes the image pickup unit.

DETAILED DESCRIPTION OF THE PREFERRED EMBODIMENT

Figure 1:
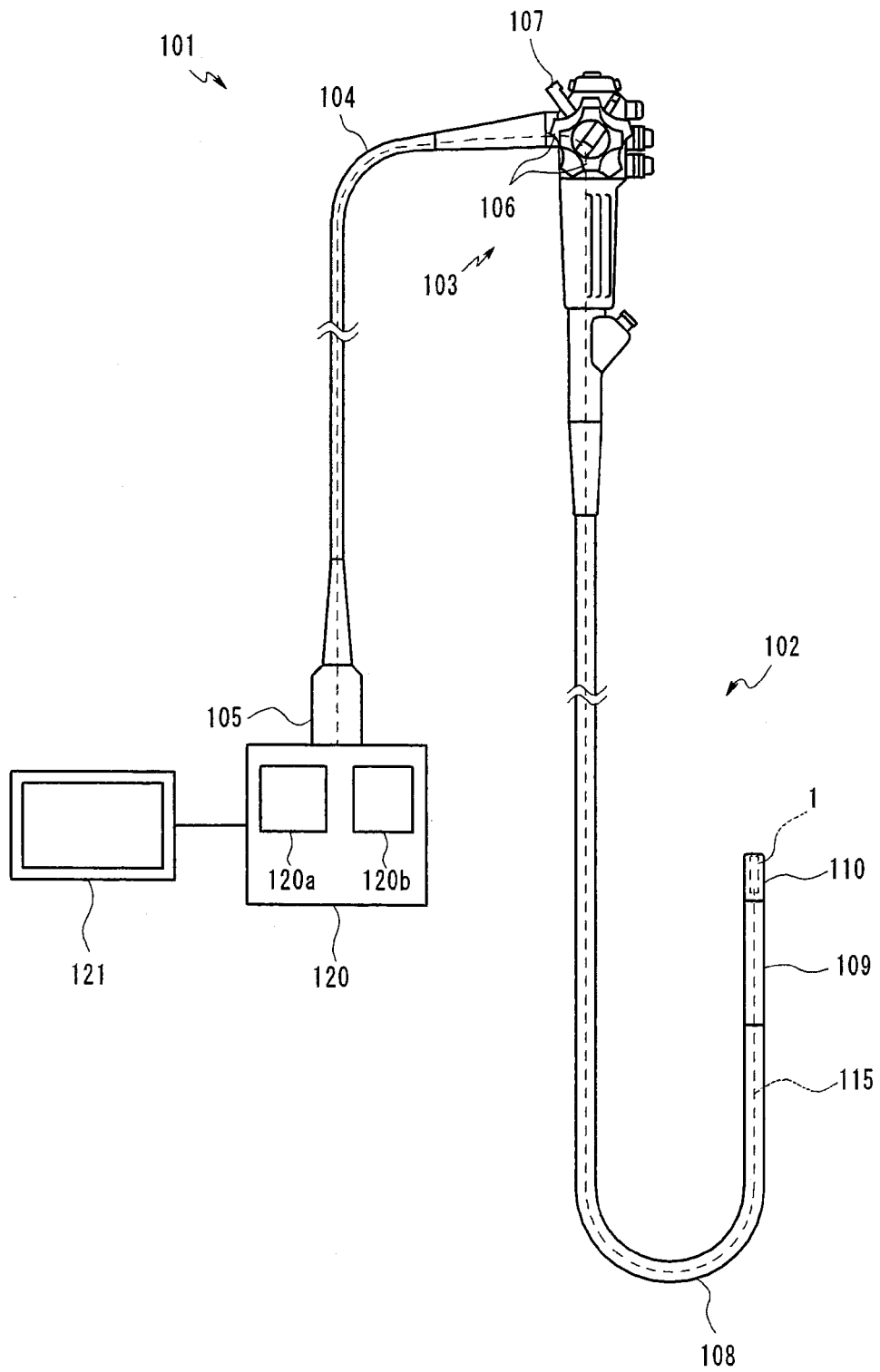
FIG. 1 is a diagram illustrating a configuration of an endoscope.

A preferred embodiment of the present invention will be described below with reference to the drawings. Note that in the respective drawings used in the below description, in order to indicate respective components in the sizes that can be recognized in the drawings, the respective components are illustrated on different scales, and thus, the present invention is not limited only to those having the numerical quantities, shapes, ratios in size between, and relative positional relationship between, the components illustrated in the drawings.

An example of an embodiment of the present invention will be described below. First, an example of a configuration of an endoscope 101 including an image pickup unit 1 according to the present invention will be described with reference to FIG. 1. The endoscope 101 according to the present embodiment has a configuration that can be introduced into a subject such as a human body and optically picks up an image of a predetermined site to be observed in the subject. Note that the subject into which the endoscope 101 is introduced is not limited to a human body, other living bodies and may be an artificial object such as a machine or a building.

The endoscope 101 mainly includes an insertion portion 102 to be introduced to the inside of a subject, an operation portion 103 positioned at a proximal end of the insertion portion 102, and a universal cord 104 extending out from a side portion of the operation portion 103.

The insertion portion 102 is configured by continuously providing a distal end portion 110 disposed at a distal end, a bendable bending portion 109 disposed on the proximal end side of the distal end portion 110, and a flexible tube portion 108 having flexibility disposed on the proximal end side of the bending portion 109 and connected to the distal end side of the operation portion 103. Note that the endoscope 101 may be one in a form including no flexible part in an insertion portion thereof, i.e., what is called a rigid endoscope.

Although a specific description will be provided later, in the distal end portion 110, an image pickup unit 1, and an illuminating light exit section 113 (not illustrated in FIG. 1) are provided. Also, at the operation portion 103, an angle operation knob 106 for operating bending of the bending portion 109 is provided. Also, at the operation portion 103, a zoom operation section 107, which is a lever switch for giving an instruction for operation of a voice coil motor section 30, which will be described later, to perform a zoom operation of the image pickup unit 1, is disposed. Note that the zoom operation section 107 may be one in any of other types such as a volume switch and a push switch.

At a proximal end portion of the universal cord 104, an endoscope connector 105 connected to an external apparatus 120 is provided. The external apparatus 120 to which the endoscope connector 105 is connected includes, for example, a light source section, an image processing section and an image display section 121.

Also, the endoscope 101 includes an electric cable 115 and an optical fiber bundle 114 (not illustrated in FIG. 1) inserted in the universal cord 104, the operation portion 103 and the insertion portion 102.

The electric cable 115 is configured so as to electrically connect the connector section 105 and the image pickup unit 1. As a result of the connector section 105 being connected to the external apparatus 120, the image pickup unit 1 is electrically connected to the external apparatus 120 via the electric cable 115. Via the electric cable 115, power is supplied from the external apparatus 120 to the image pickup unit 1 and communication between the external apparatus 120 and the image pickup unit 1 is performed.

In the external apparatus 120, a motor driving control section 120a and an image processing section 120b are provided. The motor driving control section 120a has a configuration that controls driving of the voice coil motor section 30 provided in the image pickup unit 1, which will be described in detail later.

The image processing section 120b has a configuration that generates a video signal based on an image pickup device output signal outputted from the image pickup unit 1 and outputs the video signal to an image display section 121. In other words, in the present embodiment, an optical image picked up by the image pickup unit 1 is displayed on the display section 121 as a video image. Note that a configuration in which the image processing section and the image display section 121 are partly or wholly disposed in the endoscope 101 may be employed.

Furthermore, the optical fiber bundle 114 is configured so as to convey light emitted from the light source section of the external apparatus 120 to the illuminating light exit section 113 of the distal end portion 110. Note that the light source section may be disposed in the operation portion 103 or the distal end portion 110 of the endoscope 101.

Figure 2:
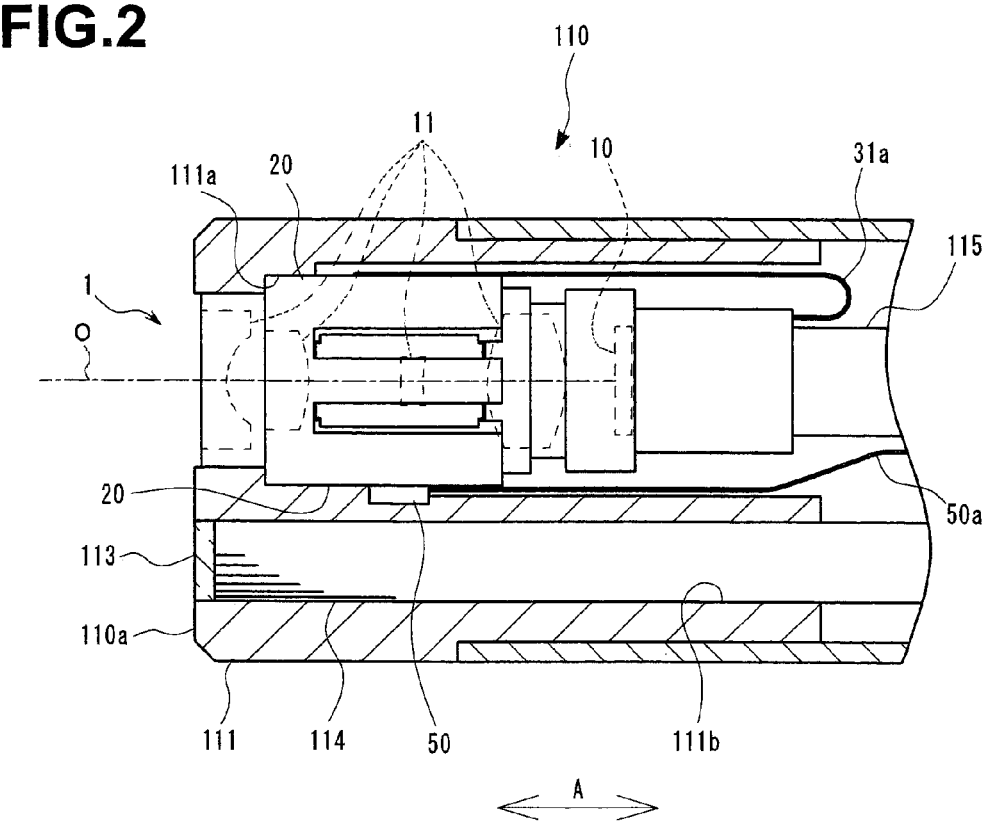
FIG. 2 is a cross-sectional diagram illustrating a schematic configuration of a distal end portion of an endoscope.
Figure 3:
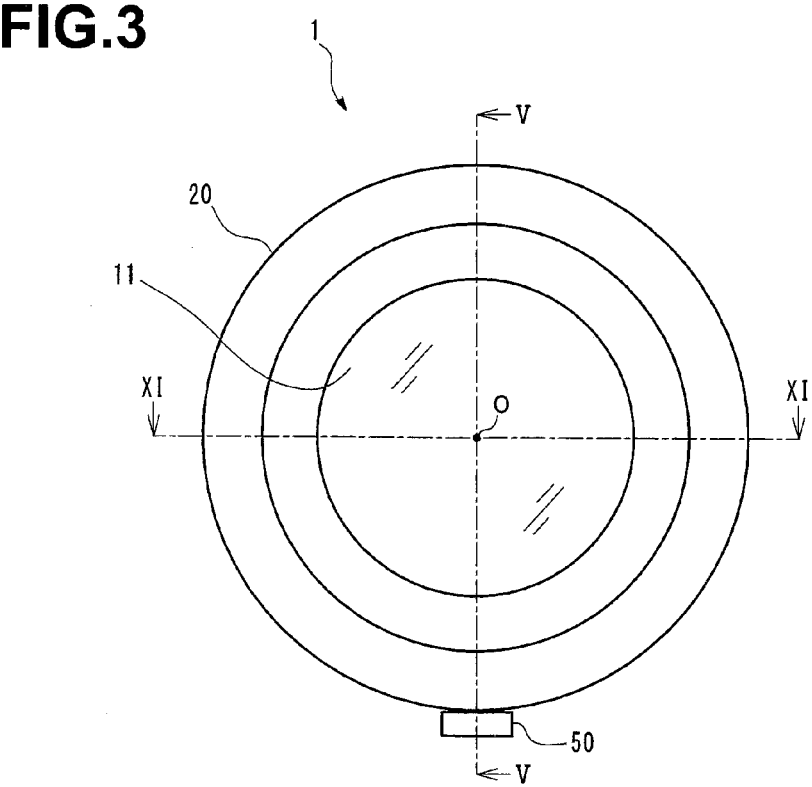
FIG. 3 is a diagram of an image pickup unit as viewed from the front along an optical axis.

Next, a configuration of the distal end portion 110 will be described. As illustrated in FIG. 2, in the distal end portion 110, the image pickup unit 1 and the illuminating light exit section 113 are disposed.

In the present embodiment, as an example, the image pickup unit 1 is disposed along a longitudinal direction (insertion axis direction) of the insertion portion 102, which is indicated by arrow A in FIG. 2, so as to pick up an image in a distal end direction. More specifically, the image pickup unit 1 is disposed in such a manner that an optical axis O of an objective lens 11 extends along the longitudinal direction of the insertion portion 102. Note that the image pickup unit 1 may be disposed in such a manner that the optical axis O forms a predetermined angle with the longitudinal direction of the insertion portion 102.

Also, the illuminating light exit section 113 has a configuration that makes light entering from the optical fiber bundle 114 exit so as to illuminate an object for the image pickup unit 1. In the present embodiment, the illuminating light exit section 113 is configured so as to make light exit from a distal end face of the distal end portion 110 in the distal end direction along the longitudinal direction of the insertion portion 102.

The image pickup unit 1 and the illuminating light exit section 113 are held by a holding section 111 provided in the distal end portion 110. The holding section 111 is a rigid member exposed at a distal end face 110a of the distal end portion 110, and includes through holes 111a and 111b provided along the longitudinal direction of the insertion portion 102. In the through holes 111a and 111b, the image pickup unit 1 and the illuminating light exit section 113 are fixed by a method such as an adhesive or screw fastening. Also, inside the through hole 111b, the optical fiber bundle 114 is inserted from the proximal end side and fixed.

Also, at a side face portion of the through hole 111a in which the image pickup unit 1 is fixed, one or more magnetism detecting sections 50 are disposed. Each magnetism detecting section 50 includes, for example, a Hall effect device or a magnetoresistive effect device (MR device), and can detect a magnetic field. The magnetism detecting section 50 is electrically connected to the motor driving control section 120a of the external apparatus 120 via a cable 50a.

Although described in detail later, inside the image pickup unit 1, two position detection magnets 39 are fixed to a moving lens holding barrel 23 that moves along the optical axis O. The magnetism detecting section 50 detects a change in a magnetic field, which occurs as a result of the two position detection magnets 39 being moved relative to the magnetism detecting section 50 in the optical axis O direction. The motor driving control section 120a calculates positions in the optical axis O direction of the position detection magnets 39, that is, a position of the moving lens holding barrel 23 based on the change in the magnetic field detected by the magnetism detecting section 50.

Figure 4:
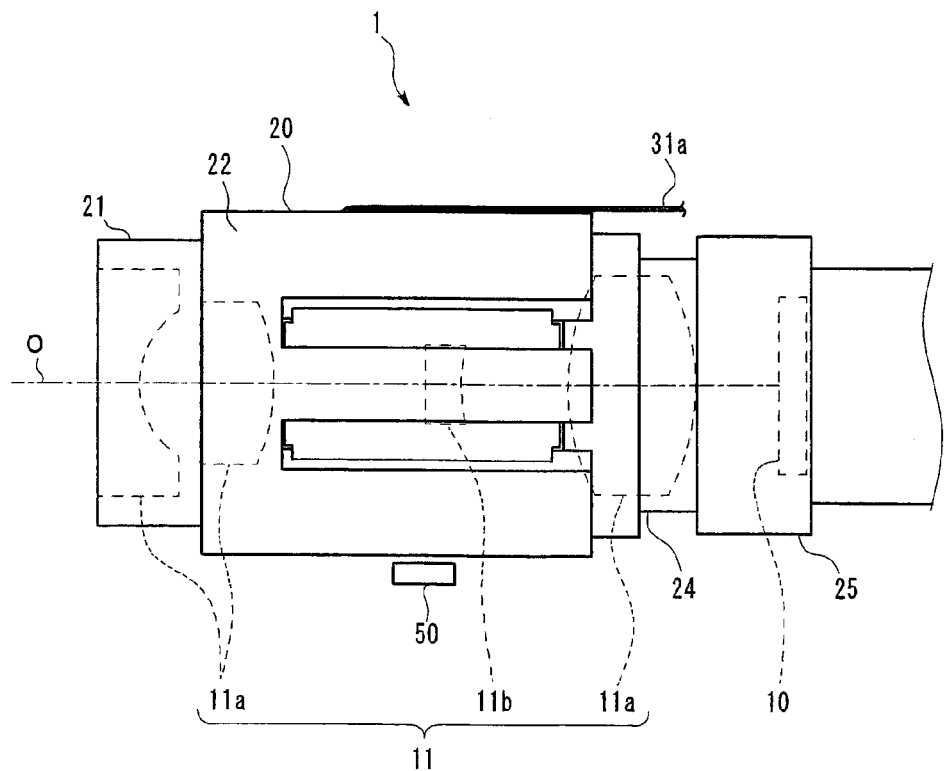
FIG. 4 is a diagram of an image pickup unit as viewed in a direction perpendicular to an optical axis.

Next, a configuration of the image pickup unit 1 according to the present embodiment will be described. As illustrated in FIG. 4, the image pickup unit 1 includes the objective lens 11, an image pickup device 10 disposed at a plane on which an image from the objective lens 11 is formed, and a lens barrel 20 holding the objective lens 11 and the image pickup device 10. Although in the present embodiment, the image pickup device 10 is disposed inside the lens barrel 20, the image pickup device 10 may be one in a form that is held by a member provided separately from the lens barrel 20.

Hereinafter, a direction from the image pickup unit 1 toward an object along the optical axis O (leftward in FIG. 4)

is referred to as "front (side)" (object side) and a direction opposite to the direction is referred to as "rear (side)" (image side).

Figure 5:
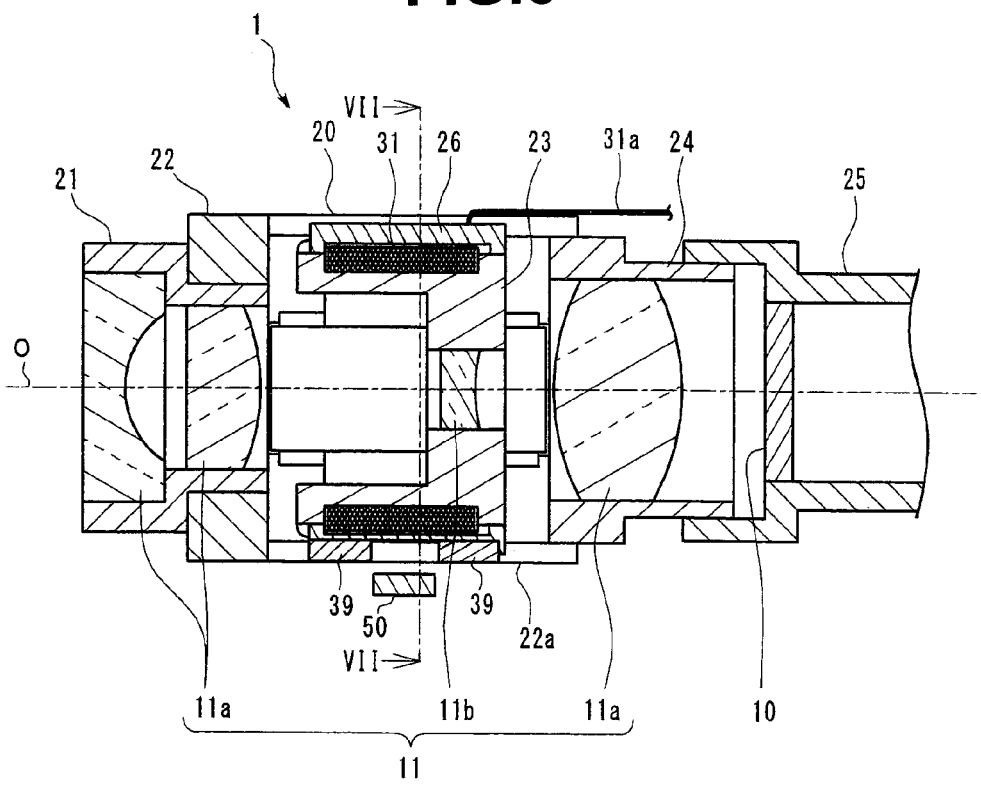
FIG. 5 is a cross-sectional view along V-V in FIG. 3.

As illustrated in the cross-sectional view in FIG. 5, the objective lens 11 includes optical system members such as a plurality of lenses through which an object image is formed. The objective lens 11 in the present embodiment includes a fixed lens 11a including one or more lenses, the fixed lens 11a being fixed inside the lens barrel 20, and a moving lens 11b including one or more lenses, the moving lens 11b being movable along the optical axis O inside the lens barrel 20, and can change an image magnification according to a position of the moving lens 11b. Such type of objective lens 11 is generally referred to as a zoom lens.

In the present embodiment, as an example, the image magnification of the objective lens 11 is largest when the moving lens 11b is positioned at a rearmost side of a movable range, and the image magnification is smallest when the moving lens 11b is positioned at a frontmost side of the movable range. In other words, a focal length of the objective lens 11, which is a zoom lens, is shortest, that is, the objective lens 11 provides a wide view field, i.e., what is called a wide end state when the moving lens 11b is positioned at the frontmost side, and the focal length is longest, that is, the objective lens 11 provides a narrow view field, i.e., what is called a tele end state when the moving lens 11b is positioned at the rearmost side.

Although the objective lens 11 according to the present embodiment is formed so as to have a smaller image magnification as the moving lens 11b is positioned closer to the front end side, the objective lens 11 may be formed so as to have a larger image magnification as the moving lens 11b is positioned closer to the front end side. Also, although in the present embodiment, the fixed lenses 11a are disposed in front of and behind the moving lens 11b, the moving lens 11b may be formed so as to be disposed on the frontmost side of the objective lens 11 or may be configured so as to be disposed on the rearmost side of the objective lens 11. Also, the entire objective lens 11 may be formed so as to be the moving lens 11b.

The image pickup device 10 is one in which a plurality of elements that each output an electric signal according to incident light at a predetermined timing are arrayed in a planer light receiving section, and for the image pickup device 10, in general, for example, an image pickup device of a type called CCD (charge-coupled device) or CMOS (complementary metal-oxide film semiconductor) sensor or any of various other types can be employed. As described above, the image pickup device 10 is disposed so that the light receiving section is positioned at the plane where an image from the objective lens 11 is formed.

Next, a configuration of the lens barrel 20 holding the objective lens 11 and the image pickup device 10 will be described with reference to FIGS. 5 and 6.

The lens barrel 20 includes a front-side lens holding barrel 21, a fixed barrel 22, a moving lens holding barrel 23, a rear-side lens holding barrel 24, an image pickup device holding barrel 25 and the voice coil motor section 30.

The front-side lens holding barrel 21, the fixed barrel 22 and the rear-side lens holding barrel 24 are each a substantially cylindrical member, and respective positions thereof are fixed via an adhesive or press fit. The front-side lens holding barrel 21, the fixed barrel 22 and the rear-side lens holding barrel 24 are members forming an outer surface, that is, a sheath of the lens barrel 20, and are fixed to the holding section 111 in the distal end portion 110 of the endoscope 1.

In the fixed barrel 22, a cylindrical portion 22a including a substantially cylindrical space inside is formed, and the later-described moving lens holding barrel 23 is fitted in the cylindrical portion 22a with a predetermined space therebetween. The moving lens holding barrel 23 is disposed so as to be slidable along the optical axis O inside the cylindrical portion 22a of the fixed barrel 22 with rotation of the moving lens holding barrel 23 around the optical axis O restricted. Also, in the fixed barrel 22, the voice coil motor section 30 that generates a drive force for moving the moving lens holding barrel 23 relative to the fixed barrel 22 is disposed. Detailed configurations of the fixed barrel, the moving lens holding barrel 23 and the voice coil motor section 30 will be described later.

Figure 6:
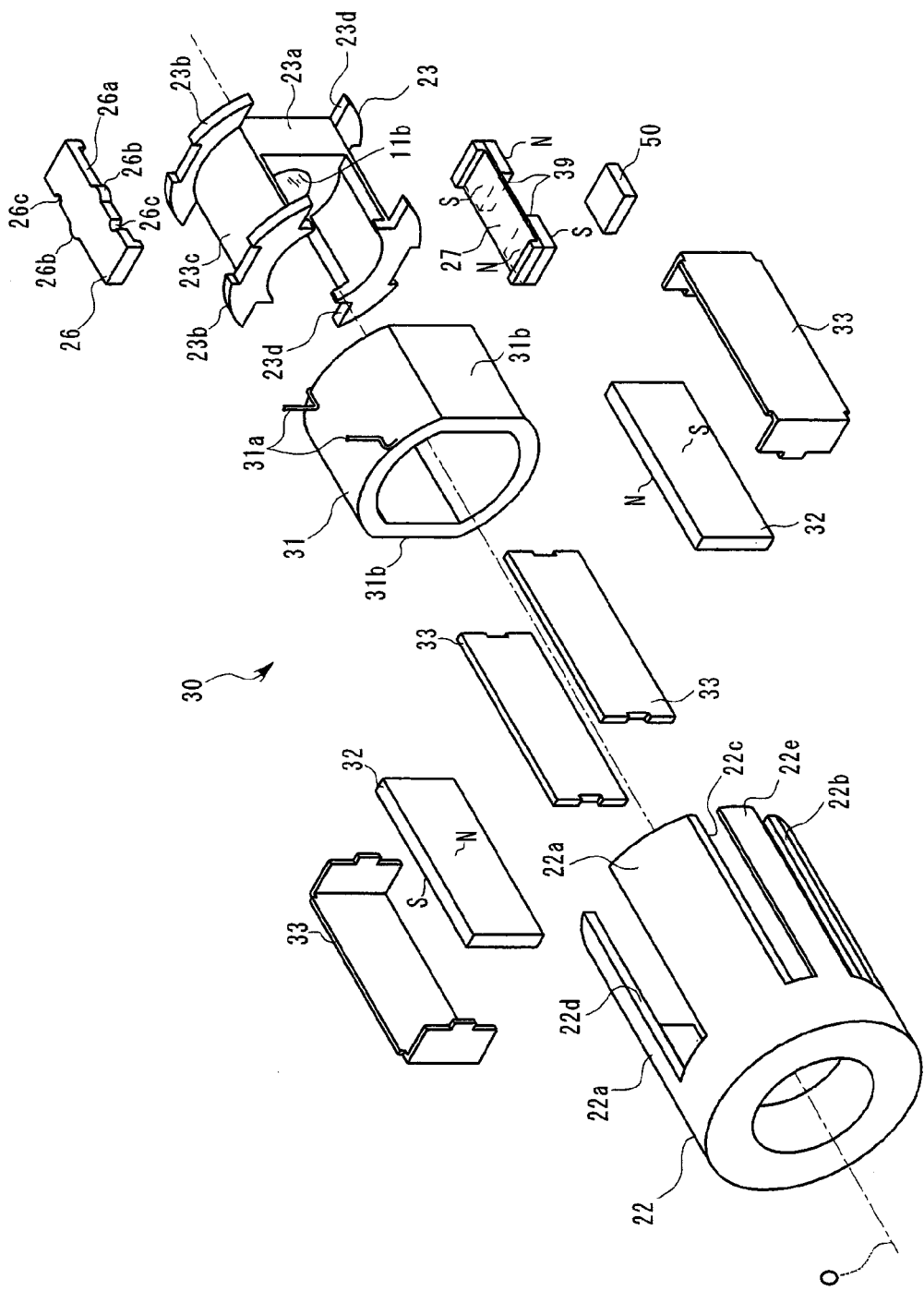
FIG. 6 is an exploded perspective view of an image pickup unit.
Figure 7:
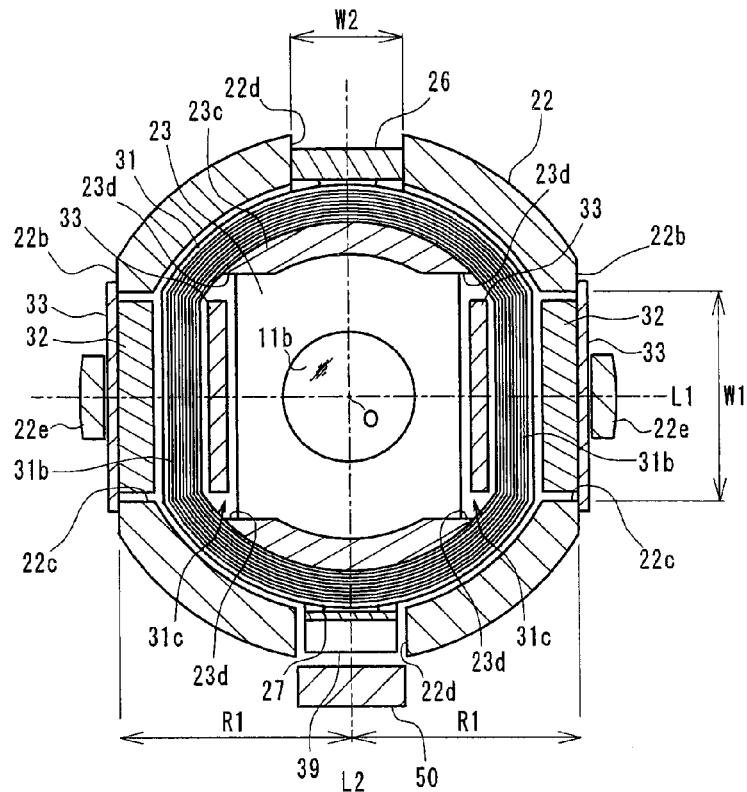
FIG. 7 is a cross-sectional view along VII-VII in FIG. 5.

Also, as illustrated in FIGS. 6 and 7, in an outer peripheral portion of the cylindrical portion 22a, a pair of flat face portions 22b that are recessed from the outer peripheral portion of the cylindrical portion 22a inward in a radial direction are formed. The pair of flat face portions 22b are provided at respective positions that are substantially parallel to the optical axis O and are a predetermined distance R1 away from the optical axis O. The pair of flat face portions 22b are provided so as to be substantially parallel to each other across the optical axis O. In other words, the pair of flat face portions 22b are provided at positions that are line-symmetrical to each other with the optical axis O as a symmetrical axis. In other words, as illustrated in FIG. 7, the pair of flat face portions 22b are a pair of flat surfaces that are each substantially perpendicular to a straight line L1 passing through the optical axis O and the predetermined distance R1 away from the optical axis O as viewed in a direction along the optical axis O.

In each of the pair of flat face portions 22b, a permanent magnet housing portion 22c is formed. The permanent magnet housing portion 22c is a slit-like part that extends through the cylindrical portion 22a in a direction perpendicular to the flat face portion 22b. The permanent magnet housing portion 22c has a shape resulting from a part with a predetermined width W1 of the cylindrical portion 22a being linearly cut out along the optical axis O. As with the pair of flat face portions 22b, the pair of permanent magnet housing portions 22c are provided at respective positions that are line-symmetrical to each other with the optical axis O as a symmetrical axis.

In other words, as illustrated in FIG. 7, the pair of permanent magnet housing portions 22c are parts that can be regarded as holes having the width W1 penetrating the cylindrical portion 22a in the radial direction with the predetermined straight line L1 passing through the optical axis O and substantially perpendicular to the pair of flat face portions 22b as a center axis thereof as viewed in the direction along the optical axis O. Also, inside each of the permanent magnet housing portions 22c, an extension portion 22e having an outer diameter that is the same as that of the cylindrical portions 22a and extending in the direction along the optical axis O is provided. As illustrated in FIG. 7, the extension portion 22e holds a permanent magnet 32 and a yoke 33 on an inner peripheral face side. With such configuration, at the time of incorporation of the yokes 33, the yokes 33 can be guided to relevant positions by the flat face portions 22b and the extension portions 22e, enabling the work for incorporating the yokes 33 to be facilitated.

Also, at positions of the cylindrical portion 22a that do not overlap the pair of flat face portions 22b, a pair of slits 22d with a predetermined width W2 penetrating the cylindrical portion 22a in the radial direction and linearly extending substantially parallel to the optical axis O are formed. The pair of slits 22d are formed at respective positions that are line-symmetrical to each other with the optical axis O as a symmetrical axis. As illustrated in FIG. 7, in the present embodiment, the pair of slits 22d are formed at respective positions shifted by 90 degrees with respect to the optical axis O from the respective positions where the pair of flat face portions 22b and the permanent magnet housing portions 22c are formed.

In other words, as illustrated in FIG. 7, as viewed in the direction along the optical axis O, each of the pair of slits 22d is a hole portion with the width W2 penetrating the cylindrical portion 22a in the radial direction with a predetermined straight line L2 passing through the optical axis O as a center axis. The straight line L2 intersects with the center axis of the pair of permanent magnet housing portions 22c substantially at right angles at the optical axis O.

The front-side lens holding barrel 21 and the rear-side lens holding barrel 24 hold respective fixed lenses 11a, and are disposed in front of and behind the fixed barrel 22. Also, the image pickup device holding barrel 25 is a member that holds the image pickup device 10 in an inner portion thereof and is fixed behind the rear-side lens holding barrel 24. Note that a configuration in which the front-side lens holding barrel 21 and the rear-side lens holding barrel 24 are partly or wholly formed integrally with the fixed barrel 22 may be employed. Also, a configuration in which the image pickup device holding barrel 25 is formed integrally with the rear-side lens holding barrel 24 may be employed.

The moving lens holding barrel 23 is a substantially cylindrical member, and holds the moving lens 11b inside. As illustrated in FIG. 6, the moving lens holding barrel 23 includes a lens holding section 23a, slide portions 23b, coil winding portions 23c, cutout portions 23d, a rotation restricting portion 26 and a position detection magnet holding section 27.

The lens holding section 23a includes a through hole provided along the optical axis O, and the moving lens 11b is fixed inside the through hole.

The slide portion 23b is a part that is fitted in the cylindrical portion 22a of the fixed barrel 22 with a predetermined space therebetween, and supports the moving lens holding barrel 23 inside the cylindrical portion 22a in such a manner that the moving lens holding barrel 23 is slidable in the direction along the optical axis O. In the present embodiment, as an example, the slide portions 23b each have a flange shape projecting outward in the radial direction from the moving lens holding barrel 23. The slide portions 23b are provided in two positions, i.e., a front-side end portion and a rear-side end portion of the moving lens holding barrel 23. Also, each of the slide portions 23b has a line-symmetrical shape with the optical axis O as a symmetrical axis. As described above, a center of support provided by the slide portions 23b that slidably support the moving lens holding barrel 23 inside the cylindrical portion 22a is positioned on the optical axis O.

Figure 8:
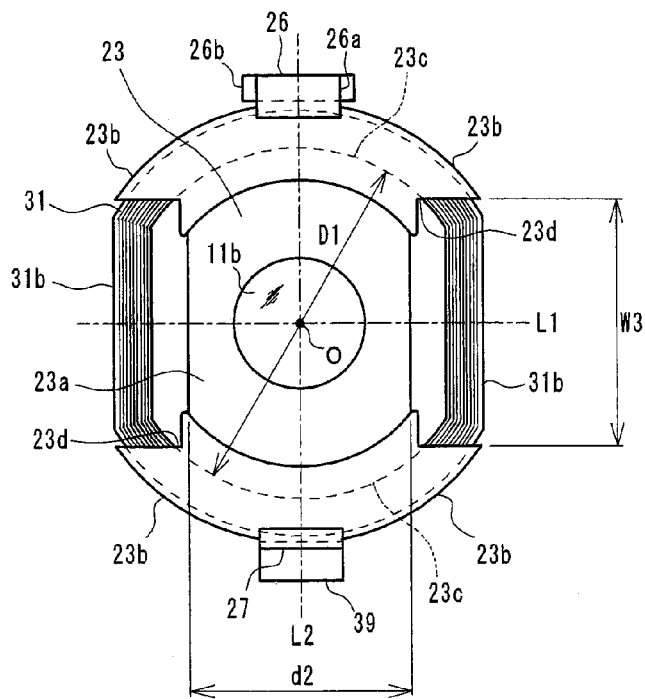
FIG. 8 is a diagram of a moving lens holding barrel as viewed from the front along an optical axis.

The coil winding portion 23c is a part on which a winding wire of a coil 31 included in the voice coil motor section 30, which will be described in detail later, is wound. FIG. 8 is a diagram of the moving lens holding barrel 23 with the coil 31 wound thereon as viewed from the front along the optical axis O. The coil winding portion 23c includes a substantially cylindrical face provided on the inner side in the radial direction relative to the slide portions 23b and has an outer diameter D1 that prevents an outer peripheral portion of the wound coil 31 from projecting on the outer side in the radial direction relative to an outer diameter of the slide portions 23b.

Also, in the moving lens holding barrel 23, the cutout portions 23d that are parts resulting from entire parts along the optical axis O of the moving lens holding barrel 23 being cut out from the outside toward the inside in the radial direction are provided. The cutout portions 23d are formed at two positions of the moving lens holding barrel 23 that are substantially equally spaced in a circumferential direction. The pair of cutout portions 23d are formed so as to have a depth allowing respective bottom face portions thereof to be positioned on the inner side in the radial direction relative to the outer diameter D1 of the coil winding portion 23c, which is a substantially cylindrical surface.

Also, the pair of cutout portions 23d are preferably provided so as to be line-symmetrical to each other with the optical axis O as a symmetrical axis. As described above, as a result of providing the cutout portions 23d to be line-symmetrical to each other with the optical axis O as a symmetrical axis, a gravity center of the moving lens holding barrel 23 can easily be positioned on the optical axis O.

More specifically, as illustrated in FIG. 8, the pair of cutout portions 23d in the present embodiment are groove portions that each have a substantially rectangular shape in cross-section and are each carved out toward the inner side in the radial direction with the predetermined straight line L1 passing through the optical axis O as a center axis so as to have a width W3 as viewed in the direction along the optical axis O. The pair of cutout portions 23d each have a flat bottom face portion substantially perpendicular to the straight line L1. In other words, the bottom face portions of the pair of cutout portions 23d are substantially parallel to each other across the optical axis O, and a distance d2 away from each other with the optical axis O as a center. The distance d2 has a value smaller than the outer diameter D1 of the coil winding portion 23c.

Although the pair of cutout portions 23d in the present embodiment each have a groove shape as viewed in the direction along the optical axis O, the pair of cutout portions 23 are not limited to those in the present embodiment and may be any of ones provided at positions symmetrical to each other across the optical axis O and each having a shape resulting from an entire part along the optical axis O of the substantially cylindrical moving lens holding barrel 23 being cut out from the outside toward the inside in the radial direction. For example, the pair of cutout portions 23d may have a shape resulting from the moving lens holding barrel 23 being cut along a pair of flat surfaces that are substantially perpendicular to the straight line L1 passing through the optical axis O and are a predetermined distance away from the optical axis O in opposite directions as viewed in the direction along the optical axis O.

The above-described moving lens holding barrel 23 has a substantially line-symmetrical shape with the optical axis O as a symmetrical axis. As illustrated in FIG. 8, the moving lens holding barrel 23, the moving lens 11b held by the moving lens holding barrel 23, the rotation restricting portion 26, the position detection magnet holding section 27 and the position detection magnet 39 are included in one unit. A gravity center of the entire unit is set so as to be penetrated by the optical axis O.

Also, in the moving lens holding barrel 23, the rotation restricting portion 26 and the position detection magnet holding section 27 are provided so as to project on the outer side in the radial direction relative to the slide portions 23b.

The rotation restricting portion 26 is a part that restricts rotation of the moving lens holding barrel 23 relative to the fixed barrel 22 around the optical axis O. The rotation restricting portion 26 projects outward in the radial direction relative to the slide portion 23b, and is fitted inside the pair of slits 22d formed in the fixed barrel 22 with a predetermined space therebetween. The rotation restricting portion 26 is provided in one of the slits 22d so as to slidable in the direction along the optical axis O.

Figure 9:
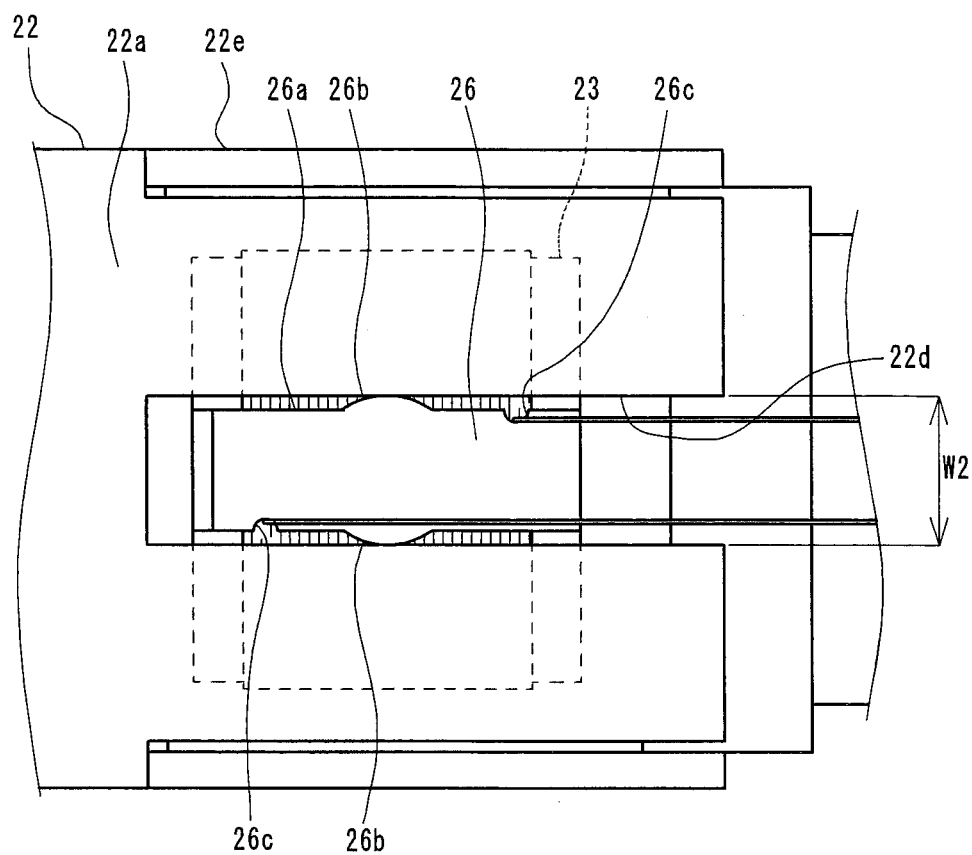
FIG. 9 is a diagram of a rotation restricting portion as viewed from the outside in a radial direction.

More specifically, as illustrated in FIG. 9, the rotation restricting portion 26 includes a beam portion 26a bridged between the pair of flange-shaped slide portions 23b provided at two positions, i.e., the front-side end portion and the rear-side end portion of the moving lens holding barrel 23, and a fitting portion 26b provided in the beam portion 26a and fitted in the one of the slits 22d.

As illustrated in FIGS. 7 and 8, the rotation restricting portion 26 projects outward in the radial direction with the predetermined straight line L2 passing through the optical axis O as a center axis as viewed in the direction along the optical axis O. Here, as described above, the straight line L2 intersects with the straight line L1, which is the center axis of the cutout portions 23d, substantially at right angles at the optical axis O.

The beam portion 26a is a plate-like member bridged between the pair of slide portions 23b, avoiding interference with the coil 31. The beam portion 26a is positioned and fixed relative to the moving lens holding barrel 23 via e.g., an adhesive or fit.

As illustrated in FIG. 9, the fitting portion 26b has a substantially circular disk shape with an axis substantially perpendicular to the optical axis O as a center axis, and projects from the beam portion 26a in a width direction. The fitting portion 26b has an outer diameter allowing the fitting portion 26b to be fitted in the one slit 22d having the width W2 with a predetermined space therebetween. Also, the fitting portion 26b is provided at a substantially center portion of the beam portion 26a. In other words, the rotation restricting portion 26 includes the substantially circular disk-shaped fitting portion 26b that is fitted in the one slit 22d at the substantially center portion between the pair of slide portions 23b so as to be slidable in the direction along the optical axis O.

As described above, in the present embodiment, as a result of the fitting portion 26b being fitted in the one slit 22d of the fixed barrel 22, rotation of the moving lens holding barrel 23 relative to the fixed barrel 22 around the optical axis O is restricted. Here, since the fitting portion 26b has a substantially circular disk shape, contact portions between inner walls of the slit 22d and the fitting portion 26b are substantially linear or point-like portions, resulting in reduction in resistance in sliding. Also, since the fitting portion 26b has a substantially circular disk shape, even if the moving lens holding barrel 23 is inclined relative to the optical axis O inside the fixed barrel 22, the resistance in sliding is maintained constant with no change occurred in the area of contact between the inner walls of the slit 22d and the fitting portion 26b, preventing sliding of the moving lens holding barrel 23 from being hindered. Also, recess portions 26c for positioning and holding lead wires 31a extending from the coil 31 are formed at side faces of the beam portion 26a.

The position detection magnet holding section 27 is a part for positioning and fixing the position detection magnets 39 relative to the moving lens holding barrel 23. The position detection magnet holding section 27 projects outward in the radial direction relative to the slide portions 23b, and projects in the other slit 22d formed in the fixed barrel 22. The position detection magnet holding section 27 holds the position detection magnets 39 so that the position detection magnets 39 are exposed at an outer periphery of the fixed barrel 22 via the other slit 22d. The position detection magnet holding section 27 is formed of a magnetic body, and serves as a yoke for the position detection magnets 39. The position detection magnet holding section 27 and the position detection magnets 39 are disposed so as not to contact with inner walls of the other slit 22d irrespective of a position of the moving lens holding barrel 23 in the fixed barrel 22.

More specifically, the position detection magnet holding section 27 is a beam-shape member bridged between the pair of flange shaped slide portions 23b provided at two positions, i.e., the front-side end portion and the rear-side end portion of the moving lens holding barrel 23. The position detection magnet holding section 27 is positioned and fixed relative to the moving lens holding barrel 23 via, e.g., an adhesive or fit.

As illustrated in FIGS. 7 and 8, the position detection magnet holding section 27 is disposed at a position shifted by 180 degrees from the rotation restricting portion 26 as viewed in the direction along the optical axis O. In other words, the position detection magnet holding section 27 is disposed on the side opposite to the rotation restricting portion 26 across the optical axis O.

On a face on the outer side in the radial direction of the position detection magnet holding section 27, two position detection magnets 39 are arrayed in the direction along the optical axis O (front-rear direction). In the present embodiment, as an example, the front-side position detection magnet 39 is disposed so that the inside in the radial direction thereof has a north pole and the outside in the radial direction thereof has a south pole, and the rear-side position detection magnet 39 is disposed so that the inside in the radial direction has a south pole and the outside in the radial direction has a north pole.

Then, a weight of the above-described rotation restricting portion 26 and a weight of the position detection magnet holding section 27 and the two position detection magnets 39 are substantially equal to each other, and a gravity center position of the rotation restricting portion 26, and a composite gravity center position of the position detection magnet holding section 27 and the two position detection magnets 39 are set in positions that are substantially line-symmetrical to each other with the optical axis O as a symmetrical axis. Accordingly, a composite gravity center of the rotation restricting portion 26, and the position detection magnet holding section 27 and the two position detection magnets 39, which are members disposed on an outer peripheral portion of the moving lens holding barrel 23, is positioned on the optical axis O.

Where the above-described moving lens holding barrel 23 is inserted into the cylindrical portion 22a of the fixed barrel 22, as illustrated in FIG. 7, the pair of cutout portions 23d provided in the moving lens holding barrel 23 are positioned in the insides in the radial direction of the pair of permanent magnet housing portions 22c provided in the fixed barrel 22.

Figure 10:
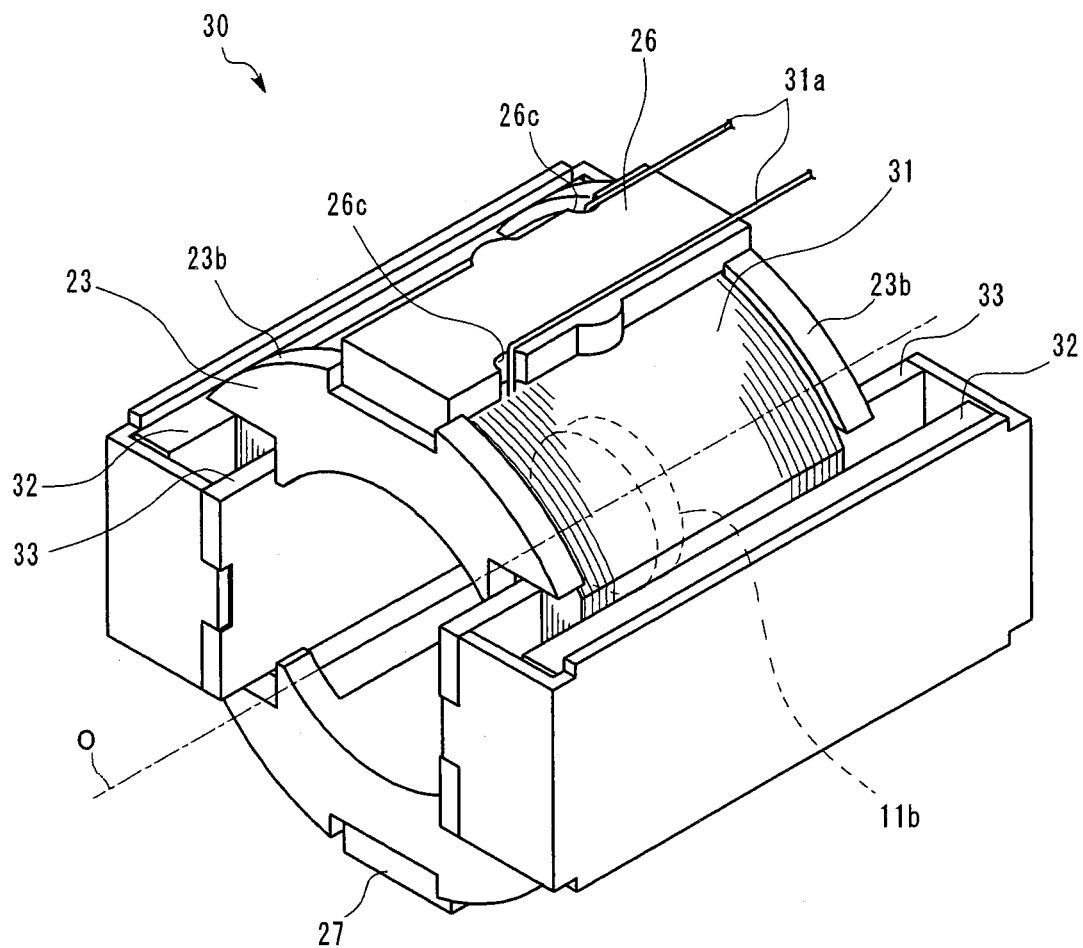
FIG. 10 is a perspective view of members included in a voice coil motor section.

Next, a configuration of the voice coil motor section 30 will be described. FIG. 10 is a perspective diagram illustrating extracted members included in the voice coil motor section 30. The voice coil motor section 30 has a configuration that generates a drive force for moving the moving lens holding barrel 23 relative to the fixed barrel 22 along the optical axis O according to an operation of the zoom operation portion 107. More specifically, the voice coil motor section 30 includes the coil 31 fixed on the moving lens holding barrel 23, the pair of permanent magnet 32 and the pair of yokes 33 fixed on the fixed barrel 22. The voice coil motor section 30 has a form of what is called a moving coil-type voice coil motor. Since the principle of voice coil motors is publicly known, a detailed description thereof will be omitted.

As described above, the coil 31 is wound around a periphery of the coil winding portion 23c provided in the moving lens holding barrel 23. Also, as illustrated in FIG. 8, as viewed in the direction along the optical axis O, the coil 31 is wound in such a manner that parts of the coil 31 positioned on the outer side in the radial direction of the pair of cutout portions 23d provided in the moving lens holding barrel 23 are substantially linear. Since the parts on which the coil 31 is linearly wound can be seen as each having a substantially plate-like shape, the parts are referred to as flat plate-like portions 31b of the coil 31 below. The coil 31 is formed so as to create respective spaces 31c with a predetermined width between the pair of flat plate-like portions 31b and the bottom face portions of the pair of cutout portion 23d. The spaces 31c provided between the flat plate-like portions 31b and the bottom face portions of the cutout portions 23d penetrate in the direction along the optical axis O.

The coil 31 is wound on the coil winding portion 23c including the pair of flat plate-like portions 31b in such a manner that the coil has a line-symmetrical shape with the optical axis O as a symmetrical axis as viewed in the direction along the optical axis O. Accordingly, a gravity center of the coil 31 is positioned on the optical axis O.

On the other hand, the pair of permanent magnets 32 and the pair of yokes 33 fixed on the fixed barrel 22 form magnetic circuits that each generate a magnetic field in a direction perpendicular to the flat plate-like portions 31b of the coil 31. More specifically, the permanent magnets 32 are disposed in the pair of permanent magnet housing portions 22c provided in the cylindrical portion 22a of the fixed barrel 22, respectively. In other words, the pair of permanent magnets 32 are disposed on the outer side in the radial direction of the coil 31 so as to face the pair of flat plate-like portions 31b, respectively. Here, in the present embodiment, as an example, each of the pair of permanent magnets 32 is disposed so that a surface on the inner side in the radial direction thereof (surface facing the optical axis O) has a north pole and a surface on the outer side in the radial direction thereof (surface opposite to the optical axis O) has a south pole.

Figure 11:
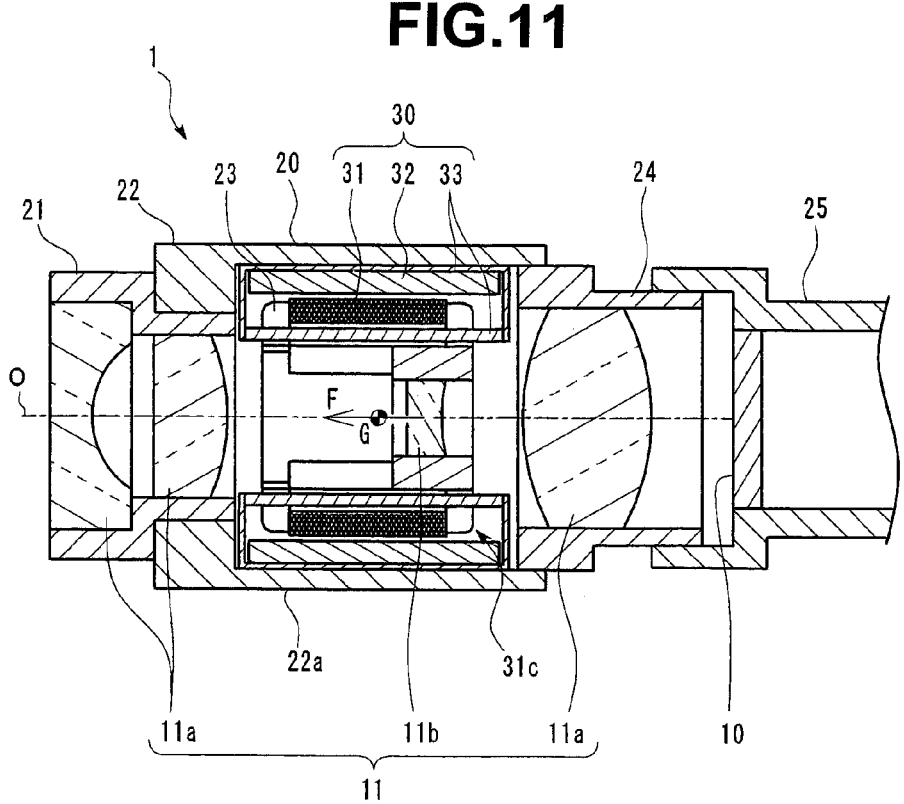
FIG. 11 is a cross-sectional view along XI-XI in FIG. 3.

Then, as illustrated in FIGS. 7, 10 and FIG. 11, on the surface on the outer side in the radial direction of each permanent magnet 32, the yoke 33 formed of a magnetic body is disposed. The yoke 33 is disposed in such a manner that the yoke 33 covers opposite ends in the optical axis O direction (front-rear direction) of the permanent magnet 32 and is inserted in the corresponding space 31c formed on the inner side in the radial direction of the coil 31. The yoke 33 is disposed so as not to interfere with the coil 31 when the moving lens holding barrel 23 moves inside the fixed barrel 22.

The yokes 33 are fixed to the respective flat face portions 22b of the fixed barrel 22 at parts positioned on the outer sides in the radial direction of the respective permanent magnets 32, via an adhesive. Also, the permanent magnets 32 are fixed to the respective yokes 33 via an adhesive or a magnetic force. The pair of permanent magnets 32 and the pair of yokes 33 are fixed at positions that are line-symmetrical to each other with the optical axis O as a symmetrical axis. Also, the pair of permanent magnets 32 and the pair of yokes 33 have respective line-symmetrical shapes with the optical axis O as a symmetrical axis.

The flat plate-like portions 31b of the coil 31 surrounded by the permanent magnets 32 and the yokes 33 as described above exist in magnetic fields in a direction perpendicular to the flat plate-like portion 31b. In other words, the permanent magnets 32 and the yokes 33 generate magnetic fields perpendicular to a direction in which the lead wire of the coil 31 is wound on the flat plate-like portions 31b. Thus, the voice coil motor section 30 according to the present embodiment can generate a drive force that makes the moving lens holding barrel 23 move along the optical axis O, by controlling current flowing in the coil 31.

In the voice coil motor section 30 in the present embodiment described above, the permanent magnets 31 are housed in the respective permanent magnet housing portions 22c that penetrate the fixed barrel 22 in the radial direction and the yokes 33 are adhered and fixed to the respective flat face portions 22b each having a shape resulting from a part of the outer peripheral portion of the fixed barrel 22 being chipped off. Thus, as illustrated in FIG. 7, when the image pickup unit 1 is viewed in the direction along the optical axis O, the permanent magnets 32 and the yokes 33 fall within a projected area of the fixed barrel 22.

Still furthermore, in the present embodiment, the cutout portions 23d are formed in respective regions of the moving lens holding barrel 22 on the inner sides in the radial direction of the permanent magnets 32, and the flat plate-like portions 31b are formed in regions of the coil 31 positioned on the outer sides of the cutout portion 23d. Since the flat plate-like portions 31b are positioned on the inner sides relative to the outer diameter of the coil 31, in the present embodiment, the permanent magnets 32 and the yokes 33 can be disposed closer to the respective inner sides in the radial direction, whereby the voice coil motor section 30 with a further reduced projected area in the optical axis O direction is provided.

Also, in the voice coil motor section 30 in the present embodiment, the pair of permanent magnets 32 and the pair of yokes 33 that generate magnetic fields, and the pair of flat plate-like portions 31b of the coil 31, which are regions positioned in the respective magnetic fields, are each disposed at positions that are line-symmetrical to each other with the optical axis O as a symmetrical axis. Thus, in the present embodiment, a center axis of action of a thrust force F generated by the voice coil motor section 30 substantially corresponds to the optical axis O. Then, in the present embodiment, a composite gravity center G of the moving lens 11b, the moving lens holding barrel 23, the coil 31, the rotation restriction portion 26, the position detection magnet holding section 27 and the position detection magnet 39, which are included in a driven member driven by a drive force by the voice coil motor section 30, are positioned on the optical axis O. Furthermore, the driven member is supported by the slide portions 23b each having a line-symmetrical shape with the optical axis O as a symmetrical axis so that the driven member can slide in the optical axis O direction inside the cylindrical portion 22a with the optical axis O as a center thereof.

As described above, in the image pickup unit 1 according to the present embodiment, a center axis of action of the thrust force F generated by the voice coil motor section 30 passes through a center of support by the slide portions 23b that support the driven member and also passes through the gravity center G of the driven member.

Accordingly, where a thrust force is applied to the driven member including the moving lens 11b by the voice coil motor section 30, the present embodiment enables the driven member to be smoothly driven along the optical axis O without the moving lens 11b being inclined relative to the optical axis O in the lens barrel 20. Thus, the driven member can be driven by the lower-power voice coil motor section 30. Various means can be considered as means for achieving downsizing of the voice coil motor section 30. For example, in the coil 31, the downsizing can be achieved by e.g., reduction in diameter of the lead wire (winding wire), reduction in number of turns of the lead wire, downsizing of the coil 31 itself (reduction in dimensions in the optical axis O direction and/or the radial direction). Also, in the permanent magnets 32 and the yokes 33, the downsizing can be achieved by e.g., reduction in thickness and/or downsizing. Downsizing of the voice coil motor section 30 enables further downsizing of the image pickup unit 1.

As described above, the present embodiment enables downsizing of the image pickup unit 1 including the moving lens 11b and the voice coil motor section 30, which is a linear actuator that drives the moving lens 11b. Also, the present embodiment enables provision of an endoscope 101 including a distal end portion 110 of an insertion portion 102 having a reduced diameter.

Also, in the image pickup unit 1 according to the present embodiment, from among the pair of position detection magnets 39 fixed to the moving lens holding barrel 23, the front-side position detection magnet 39 is disposed so that the inside in the radial direction thereof has a north pole, and the rear-side position detection magnet 39 is disposed so that the inside in the radial direction thereof has a south pole. On the other hand, each of the pair of permanent magnets 32 in the voice coil motor section 30, which is fixed to the fixed barrel 22, is disposed so that the inside in the radial direction thereof has a north pole.

Figure 12:
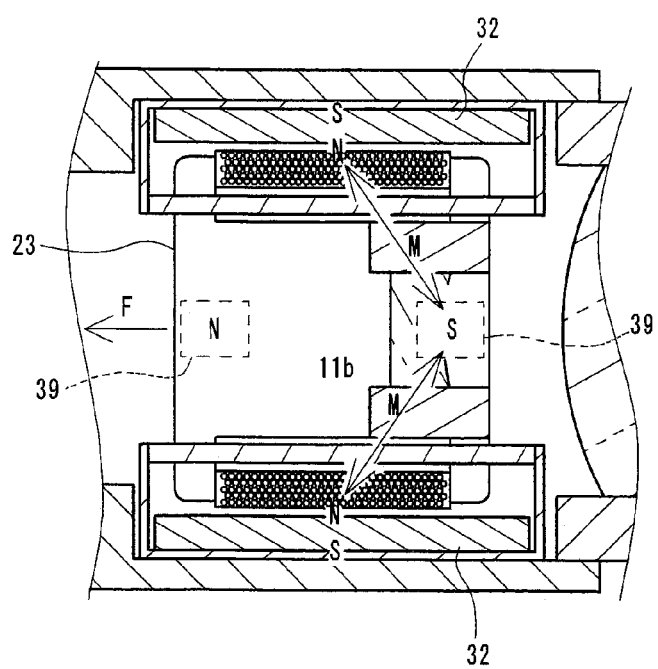
FIG. 12 is a diagram for describing action between a permanent magnet and position detection magnets.

Accordingly, as illustrated in FIG. 12, between the position detection magnet 39 (south pole) disposed on the rear side of the moving lens holding barrel 23 and the pair of permanent magnets 32 (north pole) fixed to the fixed barrel 22, attraction forces in a direction in which the position detection magnet 39 and the pair of permanent magnets 32 are mutually attracted by magnetic forces, which are indicated by arrows M. In other words, in the image pickup unit 1 according to the present embodiment, the magnetic forces between the position detection magnet 39 and the permanent magnets 32 bias the moving lens holding barrel 23 toward a front-side end portion, which is one of end portions in the movable range, as indicated by arrow F.

Here, as described above, the objective lens 11 is configured so that as the moving lens 11b is closer to the front-side end portion, the image magnification is lower. Accordingly, in the present embodiment, the position detection magnet 39 biases the objective lens holding barrel 23 by magnetic forces between the position detection magnet 39 and the permanent magnets 32 so that the objective lens holding barrel 23 moves in a direction in which the image magnification of the objective lens 11 becomes lower.

Therefore, in the image pickup unit 1 according to the present embodiment, when no current flows in the coil 31, the moving lens 11b automatically moves in the direction in which the image magnification of the objective lens 11 becomes lower (the view field becomes wider) by magnetic forces between the position detection magnet 39 and the permanent magnets 32. As described above, the image pickup unit 1 according to the present embodiment is configured so that, for example, if it becomes impossible to drive the voice coil motor section 30 because of a failure such as disconnection of the lead wire 31a, the image magnification of the image pickup unit 1 is lowered, the view field is widened and a focal depth is increased automatically, which facilitates a response to a failure. Also, for example, if the voice coil motor section 30 is made to enter a non-conducive state to transport the endoscope, unexpected damage occurred as a result of the moving lens 11b being moved by transportation motion and hit and broken can be prevented.

It is indisputable that the position detection magnets 39 and the permanent magnets 32 may have respective polarities opposite to those in the present embodiment. Also, if the objective lens 11 is configured so that as the moving lens 11b becomes closer to the rear-side end portion, the image magnification becomes lower, the position detection magnet 39 and the permanent magnets 32 are disposed so as to bias the moving lens holding barrel 23 by means of magnetic forces to move rearward.

The present invention is not limited to the above-described embodiment and can arbitrarily be modified without departing from the spirit or the idea of the invention, which can be read from the claims and the entire description, and an image pickup unit and an endoscope with such change also fall within the technical scope of the present invention.

What is claimed is:

1. An image pickup unit including an objective lens including a plurality of optical system members via which an object image is formed, the image pickup unit comprising:
    a moving lens including one or more lenses, the moving lens forming a part of the objective lens;
    a fixed lens holding barrel that holds the optical system members other than the moving lens in the objective lens;
    a cylindrical fixed barrel fixed to the fixed lens holding barrel with an optical axis of the objective lens as a center axis;
    a moving lens holding barrel that holds the moving lens and is disposed so as to be slidable along the optical axis inside the fixed barrel; and
    a voice coil motor section that generates a drive force for moving the moving lens holding barrel relative to the fixed barrel along the optical axis;
    a position detection magnet fixed to the moving lens holding barrel; and
    a magnetism detecting section whose position relative to the fixed barrel is fixed, the magnetism detecting section detecting magnetism of the position detection magnet,
    wherein the voice coil motor section is disposed so that a center axis of action of a generated thrust force passes through a gravity center of a driven member to be driven by the voice coil motor section;
    wherein the objective lens is configured so that an image magnification thereof is changed as a result of the moving lens holding barrel being moved in the optical axis direction and as the moving lens holding barrel becomes closer to one end of a movable range, the magnification becomes lower;
    wherein the voice coil motor section includes a coil wound on a periphery of the moving lens holding barrel around the optical axis, and a permanent magnet fixed to the fixed barrel; and
    wherein the position detection magnet is disposed so as to bias the moving lens holding barrel toward the one end of the movable range via a magnetic force between the position detection magnet and the permanent magnet.

2. The image pickup unit according to claim 1, wherein the voice coil motor section includes permanent magnets;
    wherein the fixed barrel includes a pair of permanent magnet housing portions that are hole portions penetrating the fixed barrel in a radial direction and housing a pair of the permanent magnets; and
    wherein the pair of permanent magnet housing portions are disposed at positions that are line-symmetrical to each other with the optical axis as a symmetrical axis.

3. The image pickup unit according to claim 2,
    wherein the moving lens holding barrel includes a pair of cutout portions each resulting from an entire portion in a direction along the optical axis of the moving lens holding barrel being cut out toward an inside in the radial direction, in regions positioned on the inner sides in the radial direction of the pair of permanent magnets; and
    wherein the coil is wound in such a manner that regions of the coil sandwiched between bottom face portions of the pair of cutout portions and the pair of permanent magnets are linear as viewed in a direction along the optical axis.

4. The image pickup unit according to claim 3, wherein in a space between each of the cutout portions and the coil, a yoke that forms a magnetic circuit jointly with the corresponding permanent magnet is inserted.

5. The image pickup unit according to claim 1,
wherein the voice coil motor section includes a coil wound on a periphery of the moving lens holding barrel around the optical axis, and a pair of permanent magnets fixed to the fixed barrel and disposed on an outer side in a radial direction of the coil;
wherein the fixed barrel includes permanent magnet housing portions that are hole portions penetrating the fixed barrel in the radial direction and housing the pair of permanent magnets; and
wherein the pair of permanent magnet housing portions are disposed at positions that are line-symmetrical to each other with the optical axis as a symmetrical axis.

6. An endoscope comprising the image pickup unit according to claim 1.

* * * * *